United States Patent [19]

Okuyama et al.

[11] Patent Number: 5,496,819
[45] Date of Patent: Mar. 5, 1996

[54] ANTIPHLOGISTIC-ANALGESIC PLASTER COMPRISING TRIACETIN AND PIROXICAM

[75] Inventors: Hirohisa Okuyama, Tomisato; Yasuo Ikeda, Narashino; Shigenori Ohtsuka, Chiba; Shuichi Kasai, Narita; Akira Iwasa, Yotsukaidoh, all of Japan

[73] Assignee: SS Pharmaceutical Co., Ltd., Tokyo, Japan

[21] Appl. No.: 211,948

[22] PCT Filed: Nov. 11, 1992

[86] PCT No.: PCT/JP92/01473

§ 371 Date: May 3, 1994

§ 102(e) Date: May 3, 1994

[87] PCT Pub. No.: WO93/09783

PCT Pub. Date: May 27, 1993

[30] Foreign Application Priority Data

Nov. 15, 1991 [JP] Japan .................... 3-300361

[51] Int. Cl.$^6$ .............. A61K 31/51; A61K 47/00; A61K 31/74; A61K 31/745
[52] U.S. Cl. ............... 514/226.5; 514/772; 424/78.02; 424/78.08; 424/78.14
[58] Field of Search ............. 424/78.02, 78.08, 424/78.14; 514/772, 226.5

[56] References Cited

U.S. PATENT DOCUMENTS

| | | | |
|---|---|---|---|
| 4,814,168 | 3/1989 | Sablotsky et al. | 424/78 |
| 5,292,461 | 3/1994 | Juch et al. | 264/37 |

*Primary Examiner*—T. J. Criares
*Attorney, Agent, or Firm*—Oblon, Spivak, McClelland, Maier & Neustadt

[57] ABSTRACT

An antiphlogistic-analgesic plaster comprising piroxicam and triacetin and/or triethyl citrate.

The antiphlogistic-analgesic plaster of the invention is excellent in percutaneous absorption of piroxicam and hence has an excellent antiphlogistic and analgesic effect.

3 Claims, 2 Drawing Sheets

ANTIPHLOGISTIC-ANALGESIC PLASTER COMPRISING TRIACETIN AND PIROXICAM

This application is filed under 35 USC 1.371 of PCT/JP92/01473 filed Nov. 11, 1992.

TECHNICAL FIELD

The present invention relates to an antiphlogistic-analgesic plaster comprising piroxicam as an active ingredient, and more particularly to an antiphlogistic-analgesic plaster improved percutaneous absorption of piroxicam contained therein.

BACKGROUND ART

Piroxicam is a compound called by a chemical name of 4-hydroxy-2-methyl-N-(2-pyridyl)-2H-1,2-benzothiazine-3-carboxamide- 1,1-dioxide and has an excellent antiphlogistic and analgesic effect. It has hence been widely used clinically at present.

Piroxicam is mostly prepared in the form of an oral preparation and in the forms of a suppository and an ointment in extreme part.

However, the oral preparation has involved a problem of side effects such as a disorder of the digestive tract. Although the side effects are somewhat reduced by the suppository compared with the oral preparation, the disorder of the digestive tract has been still recognized on the suppository. Moreover, these preparations have been difficult to effectively deliver their active ingredients to the diseased area. The ointment by which piroxicam can be topically applied has been proposed in order to remedy the above drawbacks involved in the oral preparation and suppository. However, this preparation has also been accompanied by drawbacks that its dose is inaccurate and its base ingredients adhere to clothes to smear them.

A plaster is the most effective form for percutaneously administering the drug to deliver it to the diseased area Japanese Patent Application Laid-Open No 316314/1989 discloses that a plaster in which lornoxicam, tenoxicam, piroxicam or sulindac is incorporated exhibit higher antiphlogistic and analgesic effect compared with a plaster in which a non-steroidal antiphlogistic-analgesic drug such as indomethacin, diclofenac, flurbiprofen or ketoprofen is incorporated. However, its effect is insufficient and it also offers a problem of physical properties as a plaster. Therefore, it is unfit for use and hence not yet provided in the clinical field under circumstances.

As described above, a satisfactory effect has not been successfully achieved even when piroxicam has been incorporated into a base for a plaster because its percutaneous absorption is poor.

Therefore, it is an object of the present invention to provide a piroxicam-containing plaster excellent in percutaneous absorption of piroxicam.

In view of the foregoing circumstances, the present inventors have carried out an extensive investigation. As a result, it has been found that triacetin and triethyl citrate have an effect of facilitating the percutaneous absorption of piroxicam, thus leading to completion of the present invention.

DISCLOSURE OF THE INVENTION

The present invention is directed to an antiphlogistic-analgesic plaster comprising piroxicam and triacetin and/or triethyl citrate.

BEST MODE FOR CARRYING OUT THE INVENTION

Figure 1:
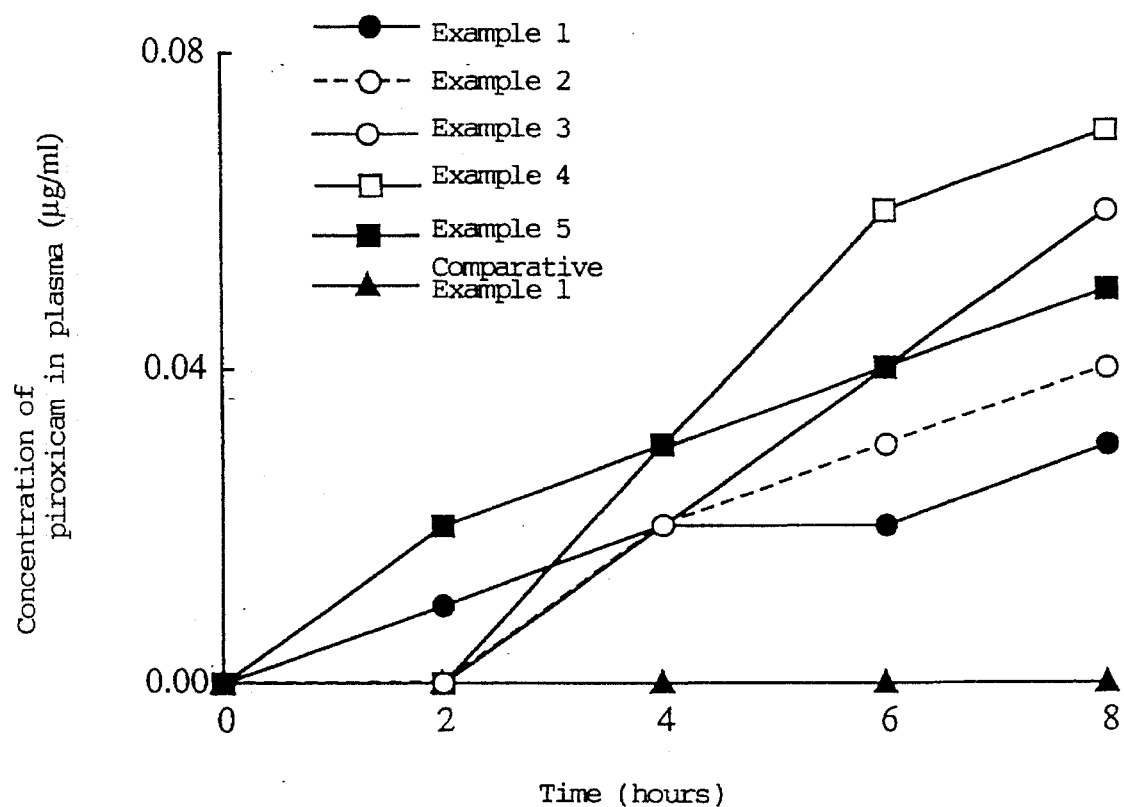
FIG. 1 is a diagram illustrating the concentration profile of piroxicam in plasma with time at the time plasters obtained in Examples 1–5 and Comparative Example 1 were separately applied to the back of a guinea pig.

In the plaster according to the present invention, the amount of piroxicam to be incorporated is preferably 0.05–5 wt. %. Besides, the amounts of triacetin and triethyl citrate to be incorporated are preferably each 0.05–40 wt. %, particularly 0.5–10 wt. %.

As base ingredients for the plaster according to the present invention, may be used base ingredients usually used. No particular limitation is imposed on such base ingredients. However, examples of the base ingredients usually used include water-soluble polymers such as sodium polyacrylate, polyacrylic acid, carboxyvinyl polymers, sodium carboxymethyl cellulose, polyvinyl alcohol and gelatin; glycols such as glycerin, propylene glycol and polyethylene glycol; cross-linking agents such as aluminum hydroxide, aluminum potassium sulfate and aluminum glycinate; purified water; inorganic powders such as kaolin and titanium oxide; pH adjustors such as citric acid and tartaric acid; surfactants such as polyoxyethylene sorbitan monooleate, sorbitan monooleate, polyoxyethylene monooleate and polyoxyethylene hydrogenated castor oil; and the like. Further, penetration enhancers, antiseptics, antifungal preservatives, antioxidants, flavorants colorants and the like may be added as needed.

Of these, the water-soluble polymers, glycols, cross-linking agents, purified water, inorganic powders and surfactants are preferably incorporated in a base in proportions of 1–20 wt. % 1–50 wt. % 0.01–5 wt. % 10–90 wt. %, 0–20 wt. % and 0–20 wt. %, respectively.

No particular limitation is imposed on the preparation process of the plaster according to the present invention. It is however prepared by a process in which a base is prepared from the above ingredients in accordance with a method known per se in the art, the base is spread on a backing material, and the surface of the spread base is covered with a protective film, or a process in which the above base is spread on a protective film, and the surface of the spread base is covered with a backing material to transfer the base to backing material.

No particular limitation is imposed on the backing material so far as it is a woven fabric, nonwoven fabric, film or sheet having good flexibility. For example, a woven fabric or nonwoven fabric from fibers of rayon, polyester, polyolefin, polyurethane or the like, polymer film, foamed sheet, or the like may be used. It is preferable to use a backing material having elasticity in all directions. An anchor coat may be applied to these backing materials as needed.

The thus-obtained plaster of the present invention is stored in a tight container or the like.

Examples

The present invention will hereinafter be described by the following examples.

Examples 1–5

Plasters having their corresponding compositions shown in Table 1 were prepared.

TABLE 1

| Example | 1 | 2 | 3 | 4 | 5 (wt. %) |
|---|---|---|---|---|---|
| Piroxicam | 0.25 | 0.25 | 0.25 | 0.25 | 0.25 |
| Glycerin | 15.00 | 15.00 | 15.00 | 15.00 | 15.00 |
| Polyoxyethylene hydrogenated castor oil | 1.00 | 1.00 | 1.00 | 1.00 | 1.00 |
| Triacetin | 0.50 | 2.00 | 4.00 | — | — |
| Triethyl citrate | — | — | — | 2.00 | 4.00 |
| Sodium carboxy-methylcellulose | 4.00 | 4.00 | 4.00 | 4.00 | 4.00 |
| Sodium polyacrylate | 5.00 | 5.00 | 5.00 | 5.00 | 5.00 |
| Gelatin | 1.00 | 1.00 | 1.00 | 1.00 | 1.00 |
| Kaolin | 4.00 | 4.00 | 4.00 | 4.00 | 4.00 |
| Aluminum glycinate | 0.15 | 0.15 | 0.15 | 0.15 | 0.15 |
| Tartaric acid | 2.30 | 2.30 | 2.30 | 2.30 | 2.30 |
| EDTA.2Na | 0.10 | 0.10 | 0.10 | 0.10 | 0.10 |
| Purified water | 66.70 | 65.20 | 63.20 | 65.20 | 63.20 |
| Total | 100.00 | 100.00 | 100.00 | 100.00 | 100.00 |

(Preparation process)

Triacetin or triethyl citrate was mixed in polyoxyethylene hydrogenated castor oil melted under heat in advance, to which piroxicam was added to stir the resultant mixture (A). Gelatin was dissolved in 40 g of purified water heated (B). Sodium carboxymethylcellulose, sodium polyacrylate and aluminum glycinate were dispersed in glycerin (C). The mixture (A), the solution (B), the dispersion (C), kaolin, tartaric acid, EDTA. 2Na and the remainder of purified water were intimately mixed with one another to obtain a base for an antiphlogistic-analgesic plaster. This paste was spread at an amount of 0.1 g/cm$^2$ on a nonwoven fabric having weight of 100 g/cm$^2$. The surface was then covered with a polyester film to obtain an antiphlogistic-analgesic plaster according to the present invention, which contained piroxicam in a proportion of 0.25 mg per cm$^2$.

Comparative Example 1

A plaster was prepared in the same manner as in Example 1 except that triacetin was not added.

Test Example 1

The plasters obtained in Examples 1–5 and Comparative Example 1 were separately applied to the shaved back (30 cm$^2$) of a male guinea pig (Hartley, aged 4 weeks, weight: 250–300 g) to collect blood through a cannule inserted in the jugular vein right before the application and upon elapsed time of 2, 4, 6 and 8 hours after the application, whereby the concentration of piroxicam in plasma was determined by a high performance liquid chromatogram to observe the concentration profile of piroxicam in plasma with time. The results are shown in FIG. 1.

Example 6

To 2 g of triethyl citrate, were added 0.25 g of piroxicam and 0.1 g of methyl para-hydroxybenzoate to intimately stir the resultant mixture (A). To 15 g of glycerin, were added 5 g of sodium polyacrylate and 0.2 g of aluminum glycinate to intimately stir the resultant mixture (B). Five grams of a carboxyvinyl polymer were dispersed in 60 g of purified water heated (C). To 10.35 g of purified water heated, were added 2 g of gelatin and 0.1 g of EDTA· 2Na to dissolve them in the purified water (D). The mixture (A), the mixture (B), the dispersion (C) and the solution (D) were intimately mixed with one another to obtain a base for an antiphlogistic-analgesic plaster. This base was spread at an amount of 0.1 g/cm$^2$ on a nonwoven fabric having weight of 70 g/cm$^2$. The surface was then covered with a polypropylene film to obtain an antiphlogistic-analgesic plaster according to the present invention, which contained piroxicam in a proportion of 0.25 mg per cm$^2$.

Comparative Example 2

A plaster was prepared in the same manner as in Example 6 except that triethyl citrate was not added, and piroxicam and methyl para-hydroxybenzoate were added to glycerol.

Test Example 2

Figure 2:
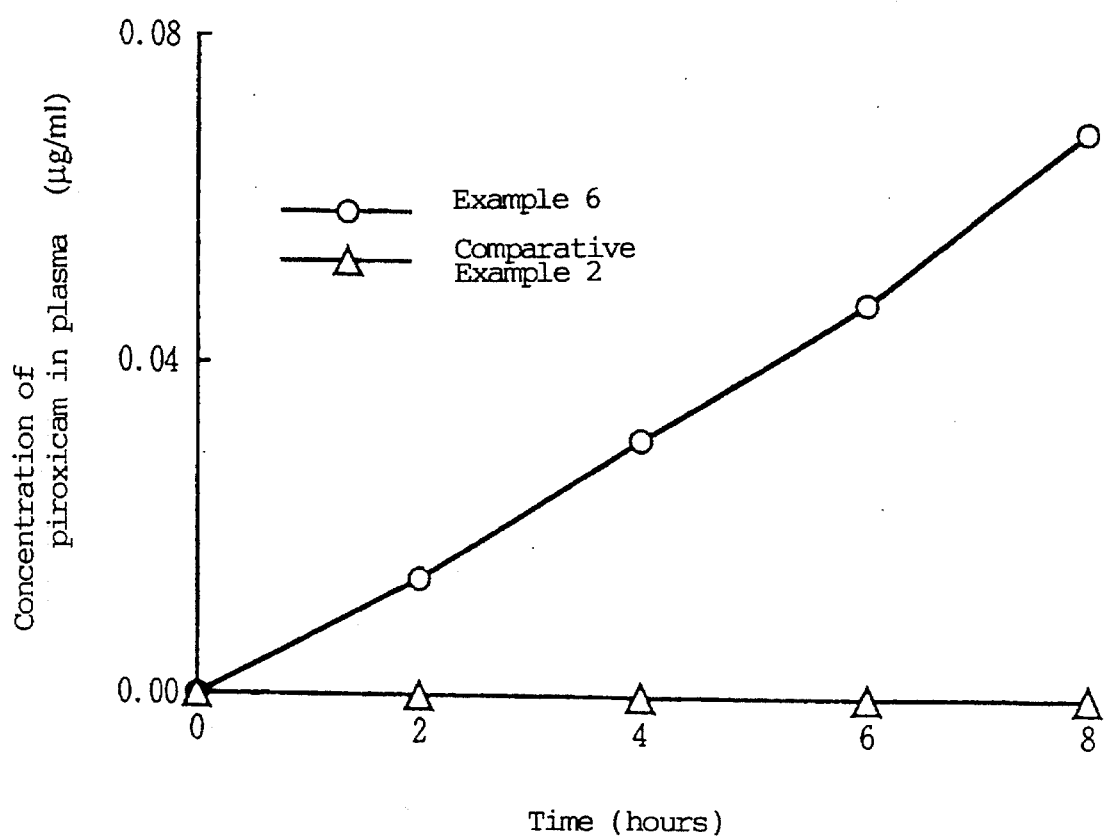
FIG. 2 is a diagram illustrating the concentration profile of piroxicam in plasma with time at the time plasters obtained in Example 6 and Comparative Example 2 were separately applied to the back of a guinea pig.

The plasters obtained in Example 6 and Comparative Example 2 were tested in the same manner as in Test Example 1. The results are shown in FIG. 2.

INDUSTRIAL APPLICABILITY

The antiphlogistic-analgesic plasters according to the present invention are excellent in percutaneous absorption of piroxicam and hence have an excellent antiphlogistic and analgesic effect.

We claim:

1. An antiphlogistic-analgesic plaster comprising 0.05–5 wt. % of piroxicam and 0.05–40 wt. % of at least one of triacetin or triethyl citrate incorporated into a plaster base, said plaster comprising a water-soluble polymer, a glycol, a cross-linking agent and water.

2. The antiphlogistic-analgesic plaster comprising piroxicam and triacetin and/or triethyl citrate as claimed in claim 1, wherein said base contains water-soluble polymers, glycols, cross-linking agents, purified water, inorganic powders and surfactants.

3. The antiphlogistic-analgesic plaster comprising piroxicam and triacetin and/or triethyl citrate as claimed in claim 2, wherein water-soluble polymers, glycols, cross-linking agents, purified water, inorganic powders and surfactants are contained in the base in proportions of 1–20 wt. %, 1–50 wt. %, 0.01–5 wt. %, 10–90 wt. %, 0–20 wt. % and 0–20 wt. %, respectively.

* * * * *

UNITED STATES PATENT AND TRADEMARK OFFICE
CERTIFICATE OF CORRECTION

PATENT NO. : 5,496,819
DATED : March 5, 1996
INVENTOR(S) : Hirohisa OKUYAMA et al.

It is certified that error appears in the above-indentified patent and that said Letters Patent is hereby corrected as shown below:

On the title page, Item [75], the third inventor's name is spelled incorrectly. It should read:

--[75] Inventors: Hirohisa Okuyama, Tomisato; Yasuo Ikeda, Narashino; Shigenori Otsuka, Chiba; Shuichi Kasai, Narita; Akira Iwasa, Yotsukaidoh, all of Japan--

Signed and Sealed this

Fourth Day of June, 1996

Attest:

BRUCE LEHMAN

*Attesting Officer*  *Commissioner of Patents and Trademarks*